United States Patent [19]

Yoon

[11] Patent Number: 4,935,027
[45] Date of Patent: Jun. 19, 1990

[54] SURGICAL SUTURE INSTRUMENT WITH REMOTELY CONTROLLABLE SUTURE MATERIAL ADVANCEMENT

[76] Inventor: Inbae Yoon, 2101 Highland Ridge Dr., Phoenix, Md. 21131

[21] Appl. No.: 396,340

[22] Filed: Aug. 21, 1989

[51] Int. Cl.$^5$ ............................................ A61B 17/06
[52] U.S. Cl. .................................... 606/146; 606/148
[58] Field of Search .............................. 606/146, 113

[56] References Cited

U.S. PATENT DOCUMENTS

| 3,807,407 | 4/1974 | Schweizer | 606/146 |
| 4,164,225 | 8/1979 | Johnson et al. | 606/146 |
| 4,244,370 | 1/1981 | Furlow et al. | 606/148 |

Primary Examiner—Randall L. Green
Assistant Examiner—Gary Jackson
Attorney, Agent, or Firm—Venable, Baetjer & Howard

[57] ABSTRACT

The invention relates to surgical instruments and methods for effecting suturing of tissue that can be controlled from a position remote from the suture site. The invention provides for the continuous feed of suture material through opposed forcep jaw members between which the tissue segments are interposed to expedite the suturing process and enable suturing to be accomplished at remote internal sites of the body incident to various endoscopic procedures.

55 Claims, 5 Drawing Sheets

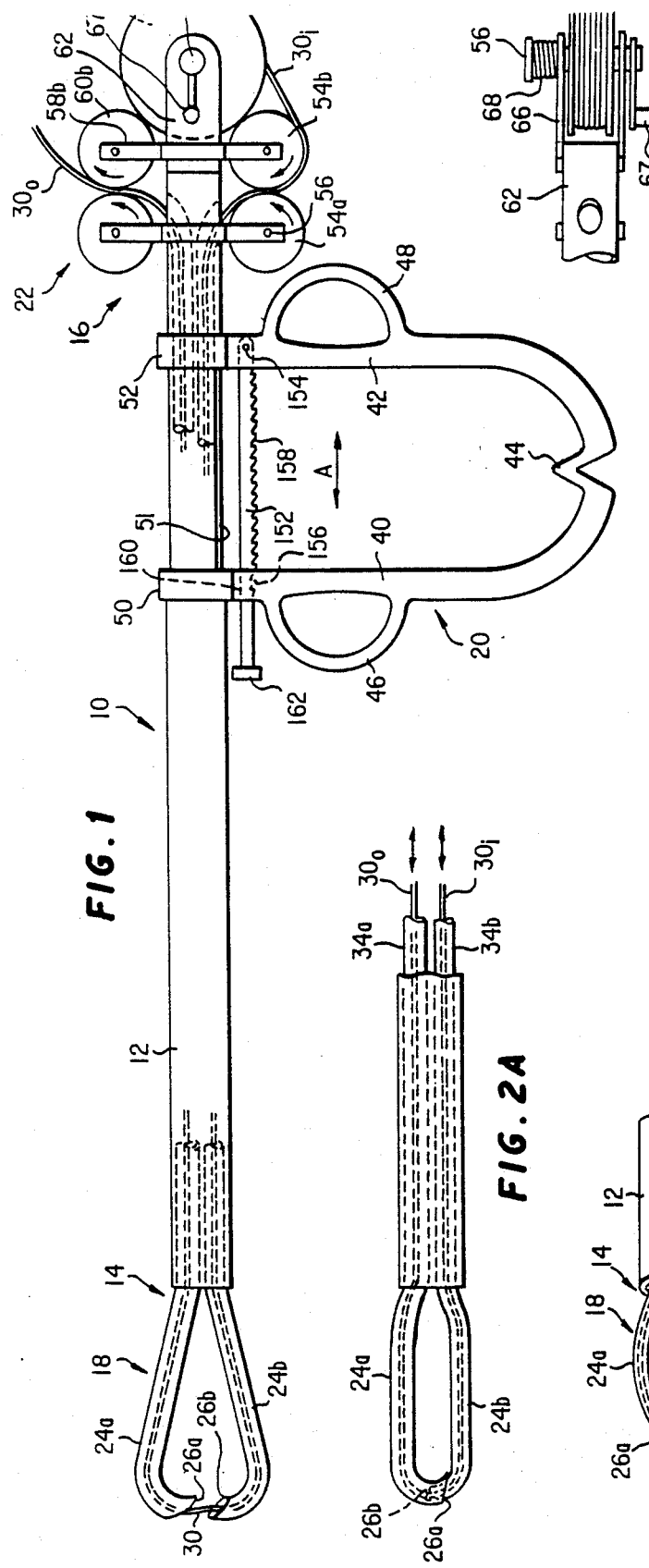

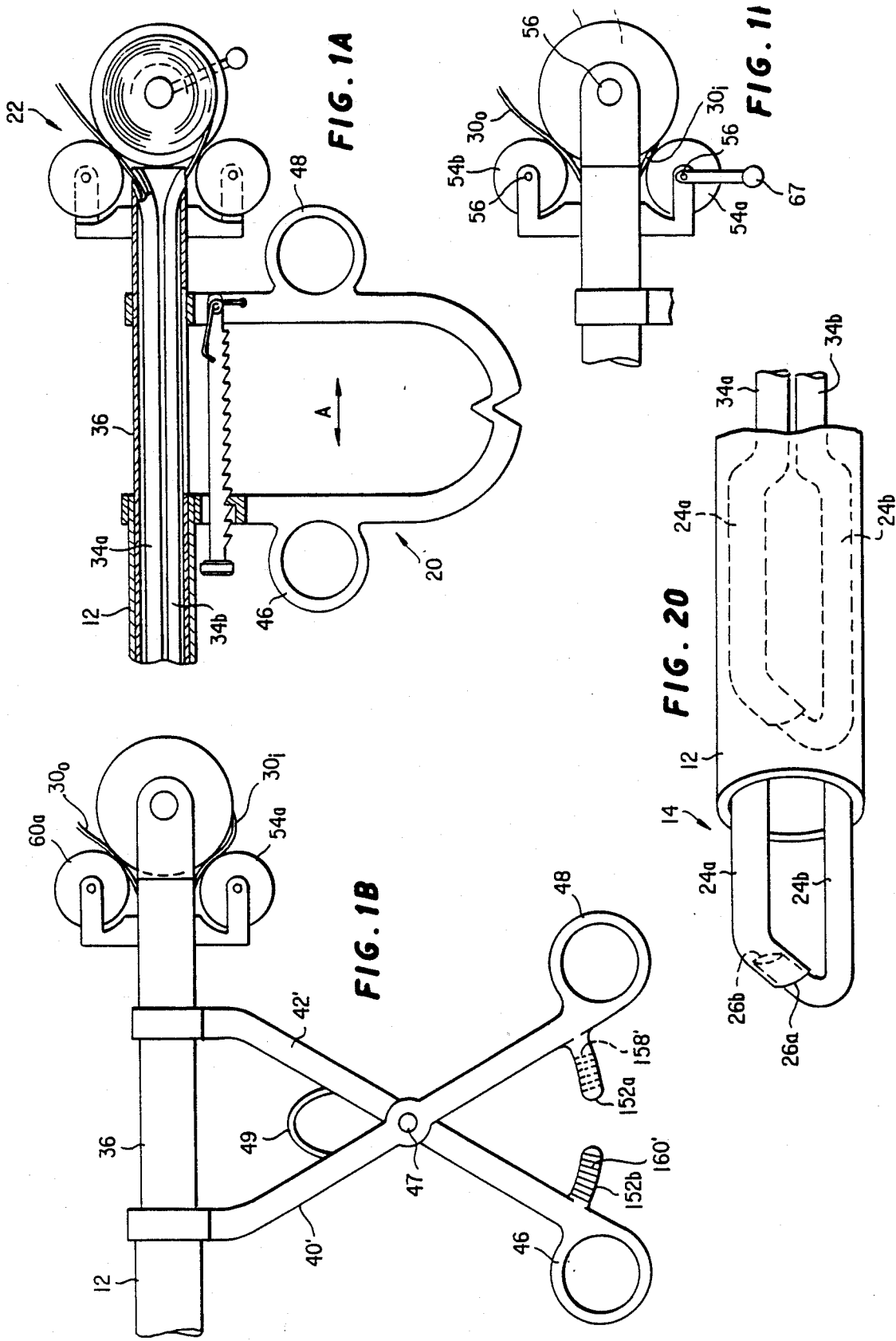

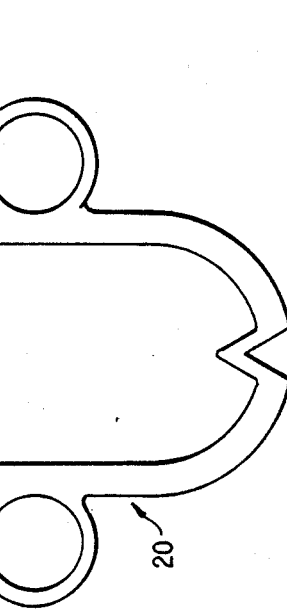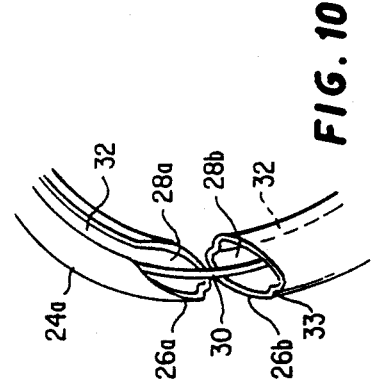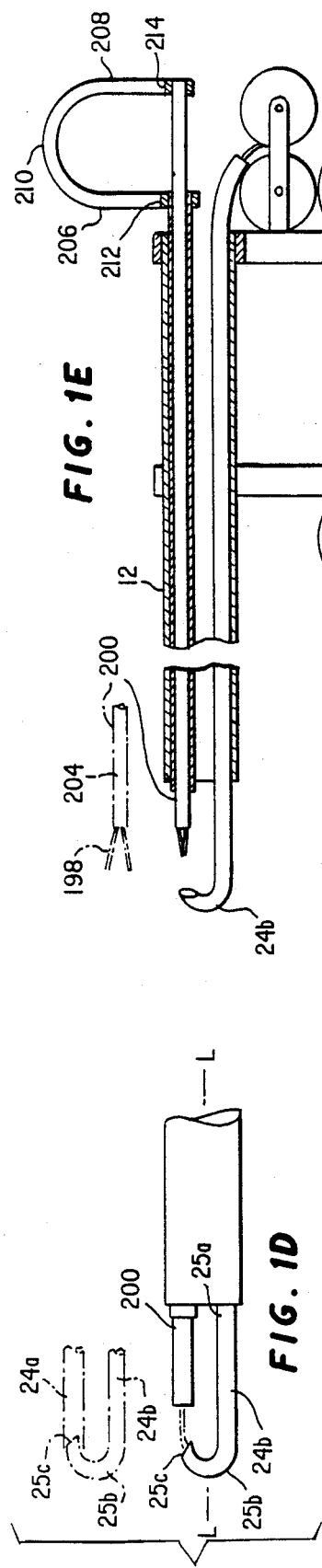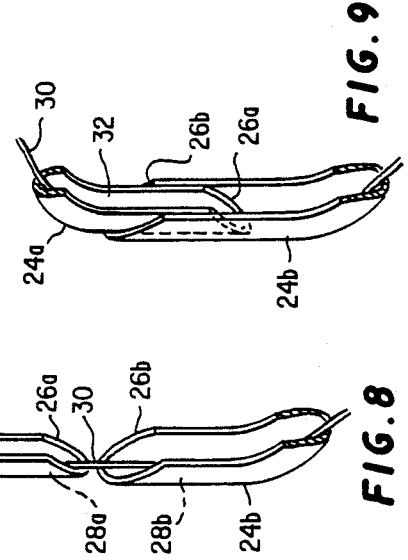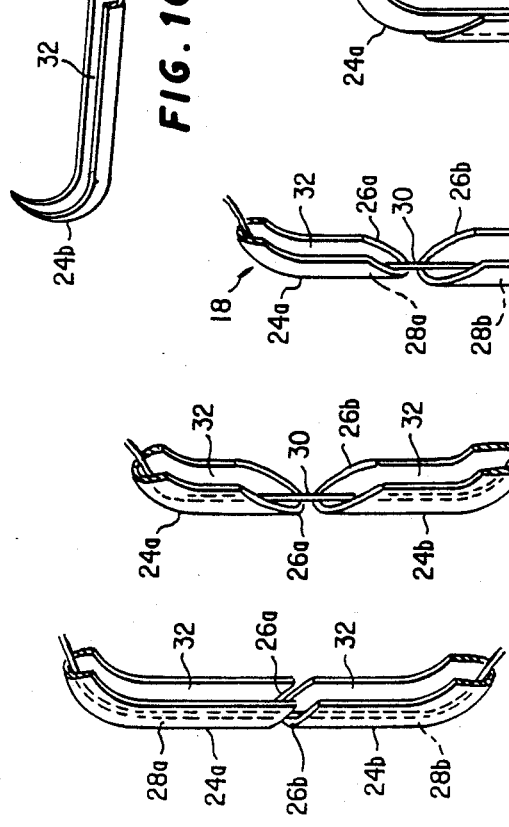

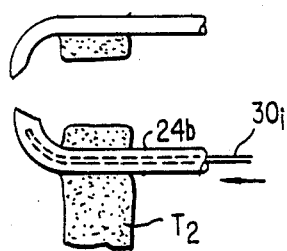
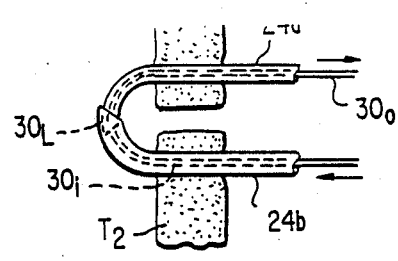
FIG. 14A    FIG. 14B
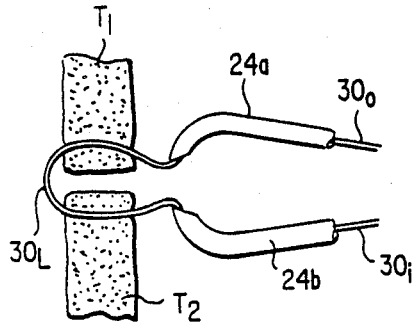
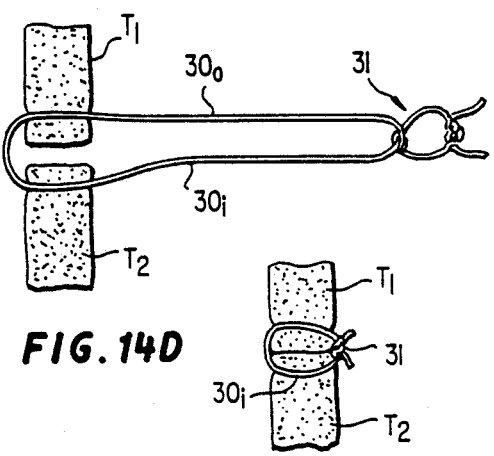
FIG. 14C    FIG. 14D
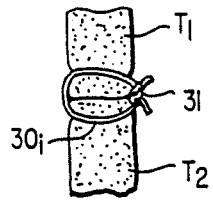
FIG. 14E
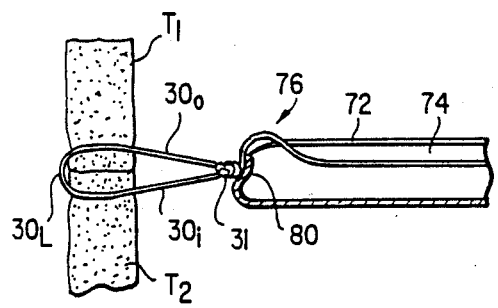
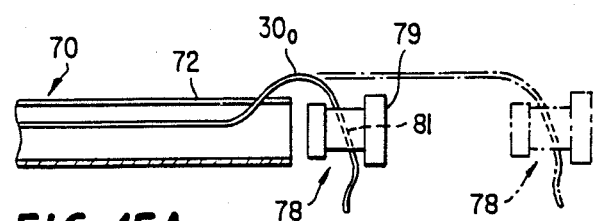
FIG. 15A
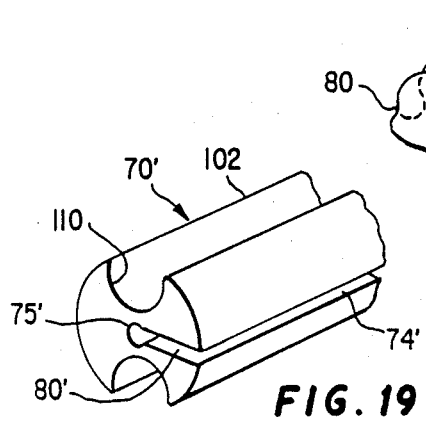
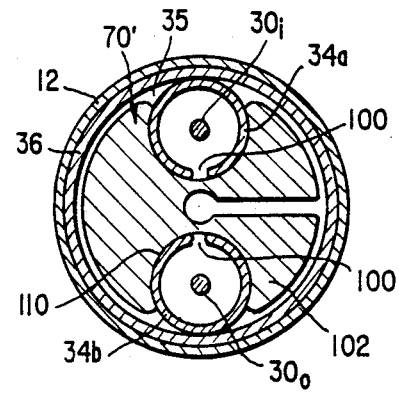
FIG. 15B
FIG. 19    FIG. 18

SURGICAL SUTURE INSTRUMENT WITH REMOTELY CONTROLLABLE SUTURE MATERIAL ADVANCEMENT

BACKGROUND OF THE DISCLOSURE

The invention relates generally to surgical instruments, and particularly to surgical instruments for suturing tissue at a surgical site. More particularly, the invention relates to surgical suturing instruments that are controllable from a position remote from the surgical site to effect tissue suturing at the surgical site.

Suturing of bodily tissue is a time consuming aspect of most surgical procedures, including both open surgery and endoscopic or closed surgery. The term "open" surgery as used herein relates to surgical procedures in which the surgeon gains access to the surgical site by way of a relatively large incision formed in an exterior portion of the patient's body. The terms "endoscopic" or "closed" surgery as used herein relate to surgery in which the surgeon gains access to a surgical site positioned beneath the surface of the patent's body by way of one or more portals through which one or more endoscopic devices can be introduced to view the surgical site. A variety of instruments such as forceps, cutters, applicators and the like can be introduced through the portals to the surgical site. Endoscopic surgery has gained popularity in recent years due to the relatively reduced degree of trauma and incapacitation associated with such procedures and the comparatively faster rates of patient recovery therefrom. Commonly performed endoscopic surgical procedures include arthroscopy, laparoscopy (pelviscopy), gastroentroscopy, and a laryngobronchoscopy.

Prior to the development of the subject suture device, suturing had been accomplished through the use of a sharp, curved metal suture needle having attached to a back end of the needle a length of suture material. The surgeon or a surgical attendant would extend the surgical needle and trailing suture material through the tissue to be joined by the suture, after which the suture material would be tied into a knot and manipulated such that the knot could be advanced to the tissue site and adjusted for tension in order to accommodate the particular type of tissue being sutured and to permit control of approximation, occlusion and attachment of the tissue. However the process of tissue penetration and knotting of the suture material can be time consuming and tedious work, particularly when performed in connection with microsurgery and endoscopic surgery, and can unduly prolong the duration of surgery, and therefore the period in which the patient is under anesthesia. Accordingly, there exists a need for surgical instruments and procedures which greatly simplify the suturing process, render more expedient suturing, and lessen the period during which the patient is under anesthesia.

SUMMARY OF THE INVENTION

The invention provides an apparatus and method which greatly simplifies surgical suturing and thereby expedites surgical procedures. The invention provides an easily manipulable surgical instrument and method in which opposed forcep jaws can be displaced relative to one another from a remotely-controlled position so as to penetrate tissue segments interposed between the forcep jaws. Suture material can be advanced from one jaw to another so as to form a connecting loop of suture material that extends between the tissue segments to be joined. The suture material is advanced in a continuous manner through the opposed forcep jaws so as to extend outwardly at or near the proximal end of the instrument. Following release of the forcep jaws, a knot can be tied in the suture material so as to join the outwardly-extending end thereof with the inlet supply of suture material, and the knot can be advanced toward the tissue segments so as to join together the tissue segments under the appropriate tension. The suture material can be any of a variety of rigid, semi-rigid, bioabsorbable or non-bioabsorbable suture material.

In an alternative aspect of the invention, the forcep jaws can be fixedly positioned relative to one another but arranged so as to provide a pathway through which suture material can be advanced so as to extend from one forcep jaw into and through the opposed forcep jaw and any one or more tissue segments interposed therebetween. Following continuous advancement of suture material through the opposed forcep jaws, a knot is tied in the suture material and advanced toward the tissue segments to be joined and appropriately tensioned to provide a suture.

BRIEF DESCRIPTION OF THE DRAWINGS

Further details of the subject invention will become apparent from a reading of the following detailed description when read in conjunction with the accompanying drawings, in which:

FIG. 1 is a longitudinal side view of a surgical suturing device in accordance with the invention;

FIGS. 1A–1F illustrate details of alternative arrangements for use in the apparatus depicted in FIG. 1;

FIG. 1G is an enlarged view of a portion of the instrument depicted in FIG. 1E.

FIGS. 2A and 2B are views of alternative arrangements of the forcep assembly of FIG. 1;

FIG. 3 is an enlarged view of the forcep assembly of FIG. 1;

FIGS. 4 and 5 are cross-sectional views of a forcep arm;

FIGS. 6–10 are alternative forcep configurations;

FIGS. 14A–14D are schematic views illustrating operation of the invention;

FIG. 15A is a side view of a suture knot advancing device that can be used various configurations of the instrument depicted in FIG. 1; and FIG. 15B is an enlarged view of the distal end of the device depicted in FIG. 15A.

FIG. 18 is a cross-sectional view of an alternative aspect of the device depicted in FIG. 16; and FIG. 19 is a perspective view of a distal portion of the device depicted in FIG. 18.

FIG. 20 is a side view of the forcer assembly depicted in FIG. 2A illustrating partial and complete retraction of the forcep within the surgical suture device.

DETAILED DESCRIPTION OF THE PREFERRED EMBODIMENTS

Figure 11:
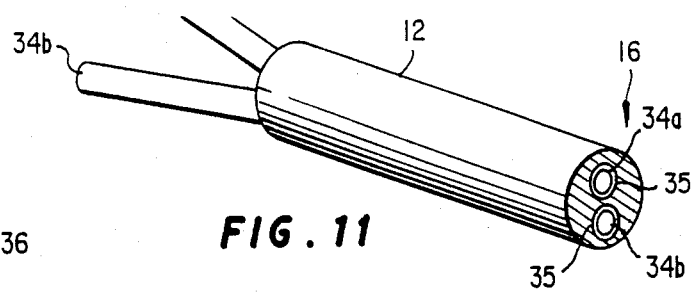
FIGS. 11 is a partial sectional view of a portion of the instrument of FIG. 1.

With reference to the drawings, wherein like reference characters designate like components throughout the various views, and with particular reference to FIG. there is depicted a suturing instrument 10 for suturing tissue at a surgical site. The suture instrument 10 comprises a tubular member 12 having a distal end 14 and a proximal end 16, a forcep assembly 18 positioned at the distal end 14 of the tube, a handle assembly 20 positioned adjacent to the proximal end of the tube, and suture advancing means 22 coupled to the proximal end of the instrument. As used throughout this disclosure, the distal end generally refers to the left-hand side of a drawing, whereas the proximal end generally refers to the right-hand side of the drawing, unless otherwise specified.

The forcep assembly 18 is comprised of a pair of opposed forcep arms 24a and 24b, each terminating at its respective distal end at a tip 26a and 26b. One or both of the forcep arms 24a, 24b can be arranged so as to be displaceable relative to the distal end 14 of the tubular member 12 to move the distal tips 26a, 26b between an open position, as illustrated in FIG. 1, and a closed position, as illustrated in FIG. 2A, or the opposed forcep arms can be fixed in position with a separation space therebetween of prescribed dimensions, as illustrated in FIG. 2B. The arms 24a and 24b of the forcep assembly can have a variety of configurations, such as the outwardly, distally curved configuration illustrated in FIG. the generally planar configuration illustrated in FIG. 2B, or a variety of other configuration as may be desirable in accordance with the tissue type to be sutured, the location of the surgical site, and other considerations.

The forcep arms 24a and 24b each define a forcep lumen 28a, 28b through which suture material 30 is extensible in a manner described in greater detail below. The forcep arms 24a and 24b can be provided with a closed cylindrical configuration, as indicated in FIG. 3, or they can be provided with a generally "C"-shaped or "U"-shaped cross-sectional configuration, as illustrated in connection with forcep arm 24a in FIGS. 4 and 5, so as to provide an open channel 32 extending the length of each of the respective forcep arms 24a and 24b. The channel openings 32 facilitate fluid drainage from the forcep assembly 18 and allow for advancement in a manner described below through the forcep assembly 18 of a suture knot (not depicted) formed in the suture material 30.

With reference to FIGS. 6–10, there is depicted a variety of configurations for approximation of the distal tips 26a, 26b of the forcep arms 24a, 24b. For example, FIG. 6 illustrates alignment and positioning of the distal tips 26a, 26b in close proximity with one another so as to contact or nearly contact one another. The distal tips 26a and 26b terminate at relatively sharp edges so as to facilitate tissue piercing upon tip approximation. As illustrated in FIG. 6, the tips 26a, 26b are angled in a complementary fashion to one another such that both forcep tips are angled distally upwardly. FIG. 7 illustrates an alternative tip configuration in which lower distal tip 26b is angled distally upwardly, whereas upper distal tip 26a is angled distally downwardly. FIGS. 8 and 9 illustrate further alternative configurations for the forcep arms and the distal tips thereof upon displacement of the forcep arms to the closed position. In FIG. 8, forcep arms 24a and 24b are configured such that arm 24a is dimensioned so as to be received within lumen 28b of the lower forcep arm 24b upon forcep arm closing, as illustrated by the phantom lines in the drawings. Furthermore, the respective distal tips are angled relative to one another in the manner analogous to that illustrated in FIG. 7. FIG. 9 illustrates an angular relationship of distal tips 26a and 26b analogous to that depicted in FIG. 6, with the exception that the upper forcep arm 24a is configured so as to be received within the lumen 28b of lower forcep arm 24b, as illustrated in phantom. FIG. 10 illustrates a further forced arm configuration, in which one forcep arm, such as forcep arm 24a, is dimensioned so as to be received within the lumen of the other forcep arm, such as lower forcep arm 24b. Respective dimensional relationships of the distal tips 26a and 26b of the respective forcep arms can be reversed such that lower forcep arm 24b is received within the lumen 28a of upper forcep arm 24a, if desired. In either arrangement of forcep arms, the distal tips 26a and 26b extend distally downwardly. This arrangement minimizes the occurrence of suture snagging or tearing upon removal of the forceps from the suture site incident to knot formation in the manner described below. The distal tips 26a, 26b of the forcep arms of any of the various forcep configurations as illustrated in FIGS. 6–10 can be provided with a tip configuration as illustrated in FIG. 10, in which the distal edge of the forcep tip is provided with a smooth umbricated or concave slot 33 that extends inwardly toward the forcep arm lumen 28a, 28b. This arrangement can be provided to further minimize the occurrence of suture material snagging and tearing from engagement with sharp edges of the distal tip that could otherwise occur in the absence of such slots 33.

A further alternative forcep arrangement is illustrated in FIGS. 1D and 1E. In this alternative forcep configuration, one of the forcep arms, such as the lower forcep arm 24a, is configured in a generally hook-shaped configuration comprising a generally distally extending leg 25a, a curved medially-extending leg 25b, and a proximally-extending leg 25c. The curved leg 25b is arranged such that it extends from one side of the longitudinal axis L of the tubular member 12 to the other side thereof so as to enable tissue segment piercing and joining by the single forcep arm 24b. In this manner, suture material can be advanced within lumen 28b of the forcep arm 24b so as to extend through all tissue segments to be joined before emerging therefrom. The suture material exiting the proximal leg 25c of the forcep arm 24b can be received by upper forcep arm 24a, which can be configured as a fixed or displaceable arm having a lumen 28a in the manner described above (FIG. 1), or as a tubular rod 200 carrying a plurality of radially extensible forcep tongues 198 (FIG. 1E) that are selectively extensible and retractable upon manipulation of handle 202 mounted at the proximal end thereof. The rod 200 is arranged as an extensible tubular member received within tubular member 12 and includes a selectively extensible and retractable inner rod 204 having mounted at its distal end the array of forcep tongues. The handle 202 is provided with a generally inverted U-shaped configuration that includes a distal arm 206 coupled to proximal arm 208 by spring arm 210. The free end 212 of handle arm 206 is coupled to the exterior of rod 200, whereas the free end 214 of handle arm 208 is coupled to rod 204 such that, upon urging of handle arms 206, 208 toward one another, rod 200 is displaced toward the proximal end of the instrument as the inner rod 204 is displaced distally to permit the forcep tongues to extend radially outwardly so as to define an opening for grasping the distal end of suture material emerging from the opposed forcep arm 24b. Upon release of handle tension, the inner rod 204 is retracted within outer the rod and the flange tongues 198 grasp firmly against the suture material to secure the suture material therebetween. Once the suture material has been grasped by the forcep tongues 198, the rod 200 can be withdrawn from tubular member 12 so as to circulate suture material through forcep arm 24b and advance the grasped free end of the suture material proximally to permit suture knot tying. Once a suture knot has been tied, the knot can be advanced to the tissue segments joined thereby in the manner described below, as by use of the aforedescribed device 70 (FIG. 15A).

The forcep arm 24b can be configured so as to be defined by a closed sidewall, as shown in FIG. 1E, or by an open-sided sidewall of generally C-shaped or U-shaped cross-sectional configuration, as shown in FIG. 1G.

Figure 12A:
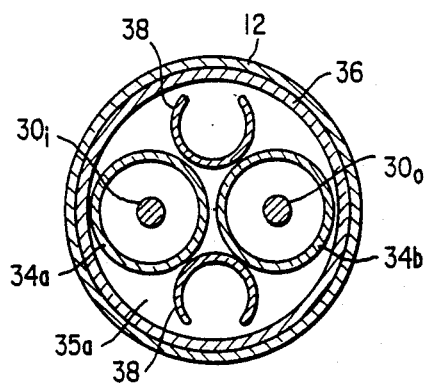
FIGS. 12A and 12B are cross-sectional views of various portions of the instrument of FIG. 1.

FIG. 11 illustrates details of the tubular member 12 of the instrument 10. The tubular member 12 is provided with a pair of inner tubular members 34a and 34b which extend from the proximal end 16 to the distal end 14 of the outer tubular member 12. The inner tubular members 34a and 34b can be in the form of tubular channels borred in a tubular member 12 that is solid in cross-section, as indicated by reference numeral 35, or they can be in the form of discrete tubular members positioned within a cavity 35a formed in the outer tubular member 12, as shown in FIG. 12A. The inner tubular members 34a and 34b are preferably arranged in axial alignment with forcep arms 24a and 24b, respectively, and are in fluid communication with the respective lumens 28a, 28b thereof so as to provide for the advancement of suture material 30 therethrough. In particular, it is desirable to advance suture material 30 from the proximal end 16 of the outer tubular member 12 through one of the inner tubular members, such as inner tubular member 34a, through the lumen 28a of the corresponding forcep arm 24a so as to extend in a continuous manner into the lumen 28b of the opposed forcep arm 24b for return passage through the other of the inner tubular members 34b proximally in this described configuration. However, it is to be appreciated that the respective directional orientations of suture material advancement can be reversed from that described above such that suture material advances from the proximal end 16 of the tubular member 12 through inner tubular member 34b so as to be conveyed through lower forcep arm 24b, through upper forcep arm 24a, and back through inner tubular member 34a for knot tying in the suture material.

In a further preferred arrangement for the outer tubular member 12, inner tubular members 34a and 34b are secured in a conventional manner to the inner wall of a middle tubular member 36 concentrically received within outer tubular member 12. A pair of tubular channel members 38 can be positioned adjacent the inner tubular members 34a, 34b so as to extend longitudinally through middle tubular member 36. The tubular channel members 38, which can be configured as closed-sided tubular channels, or as generally "C"-shaped or open-sided channels as shown, provide for the circulation of fluid to and from the surgical site, as well as for the insertion therethrough of one or more auxiliary surgical instruments such as fiber optic and other imaging, treatment or diagnostic apparatus, and can be permanently or detachably mounted to the middle tubular member 36. Detachable mounting of the channel members 38 can be advantageous when preparing the surgical instrument 10 for sterilization following use on a patient or when the channel members are arranged to be disposable and replaceable by replacement channel members formed from a suitable material, such as plastic. In this and subsequent drawings, extension of the suture material 30 through the respective inner tubular members 34a and 34b is directionally oriented such that advancement of the suture material toward the forcep assembly 18 is designated 30i (inlet), whereas return of the suture material therefrom is designated as 30o (outlet). As noted previously, the respective directional orientations of advancement of the suture material through inner tubular members 34a and 34b can be reversed from that described herein, if desired.

Figure 12B:
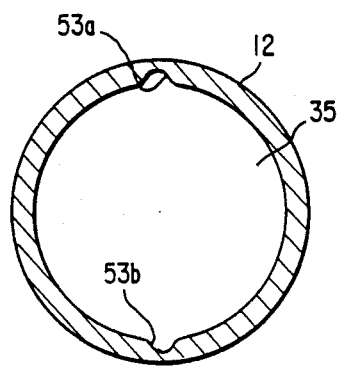

With reference again to FIG. 1, the handle assembly 20 includes a distal arm 40 joined to a proximal arm 42 through a spring member 44. Handling rings 46 and 48 are provided such that ring 46 is mounted to distal arm 40 and ring 48 is mounted to proximal arm 42. The handling rings 46, 48 are dimensioned so as to receive one or more fingers of a user so as to facilitate relative displacement of the handle arms 40, 42 inwardly or outwardly, as indicated by the arrow A, and can be provided with a variety of different configurations, such as half-circular (FIG. 1) or annular (FIG. 1A). The shoulder 50 (FIG. 1) of distal arm 40 extends through slot 51 formed in the outer tubular member 12 to engage the inner tubular members 34a and 34b either directly or by way of engagement with middle tubular member 36 (FIG. 12A). The shoulder 52 of proximal handle arm 42 is coupled to the outer tubular member 12 such that movement of the handle arms 40 and 42 toward one another results in proximal displacement of forcep arms 24a and 24b so as to close the respective tip portions 26a and 26b toward one another as the forcep arms are retracted within distally extending outer tubular member 12. The forcep assembly can be arranged so as to be partially or fully retracted within outer tubular member 12, as shown in solid lines and in phantom, respectively, in FIG. 20. Slots 53a, 53b can be formed along the interior surface of the distal portion 14 of the outer tubular member 12, as shown in FIG. 12B, to provide a guiding structure along which the proximally-displaced portions of the forcep arms 24a, 24b can slide incident to closure or approximation to facilitate retraction (and extension) of the forcep assembly relative to the outer tubular member during forcep arm manipulation through the handle assembly 20. Displacement of the handle arms 40 and 42 away from one another, as would occur upon the release of the compressive force stored in the spring member 44 generated by the movement of the handle arms 40 and 42 toward one another, results in proximal movement of the outer tubular member and simultaneous distal movement of inner tubular members 34a and 34b (and any surrounding middle tubular member 36 that may be present) so as to release and extend the forcep arms 24a and 24b to the open position illustrated in FIG. 1.

The relative position of handle arms 40 and 42 can be fixed by selective engagement of locking mechanism 150 so as to correspondingly fix the relative positions of the opposed forcep arms 24a and 24b. The locking mechanism 150 includes an arm or bar 152 pivotably mounted to one of the handle arms such as arm 42, by pivot means such as pivot pin 154, that extends through a slot 156 formed in the other handle arm 40. The lock arm 152 can be configured as a gear rack having a plurality of angled or ratchet-like protrusions 158 formed along a portion of the exterior surface of the arm that are selectively engageable with corresponding, complementary-angled or ratchet-like protrusions 160 formed along one of the sides of the slot 156 upon rotatable manipulation of the lock arm 152 by handle 162 so as to bring the respective arm and slot protrusions 158, 160 into juxtaposition. Locking of the handle arms can be advantageous so as to free the user's hands to operate further components of the instrument, such as the suture material advancing means 22 described below, or to operate other equipment related to the surgical procedure to be used in conjunction with, or independently of, the instrument 10.

In an alternative arrangement, the handle 20 can be configured as a scissor-like handle, as illustrated in FIG. 1B, in which the distal and proximal arms 40' and 42' are pivotably coupled to one another at pivot 47 and are resiliently biased by spring means 49 in a position so as to orient the forcep arms 24a, 24b coupled thereto in any of the manners described above in a predetermined position. For example, coupling of distal scissor arm 40' to outer tubular member 12 and proximal scissor arm 42' to inner tubular member 34a, 34b either directly or through middle tubular member 36, as shown, predisposes the forcep arms to maintain in an open (separated) position until the handle arms 40', 42' are urged toward one another against the force exerted by spring means 49. The handle arms 40', 42' can be locked together in a selected position through engagement of mutually engageable locking arms 152a, 152b and their respective, correspondingly-configured engagement surfaces 158', 160' as described above in connection with the locking arrangement depicted in FIG. 1.

Figure 13:
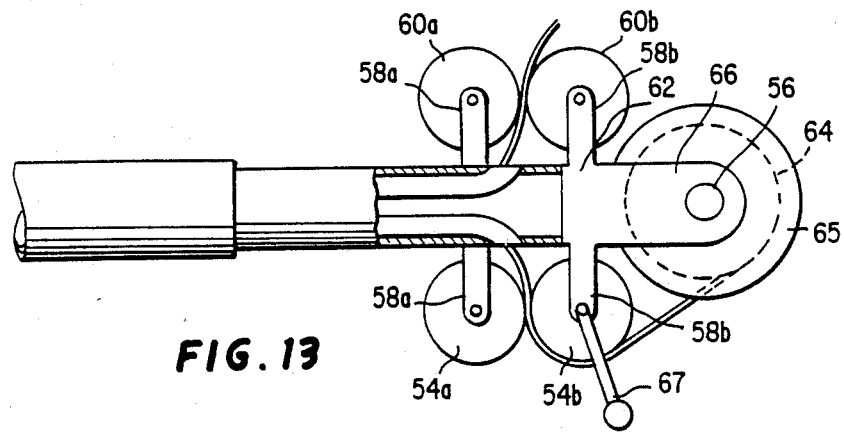
FIG. 13 is a detailed side view of a portion of the instrument of FIG. 1.

With reference to FIGS. 1 and 13, the suture material advancing assembly 22 positioned at the proximal end 16 of the outer tubular member 12 comprises a pair of inlet guide rollers 54a, 54b pivotably mounted by pins 56 to support arms 58a and 58b, respectively. Positioned opposite the inlet guide rollers 54a and 54b is a pair of outlet guide rollers 60a and 60b mounted by pins 56 to support arms 58a and 58b, respectively. The support arms 58a and 58b are, in turn, are-mounted to a support rod 62 which is coupled at its distal end to the outer tubular member 12 at shoulder 52. The support rod 62 can be disengageably-mounted with respect to the outer tubular member 12 to permit its removal therefrom incident to replacement, cleansing and sterilization of the instrument, as well as to permit for the insertion of various supplemental instruments through the cavity 35 of the outer tubular member. Alternatively, the support rod 62 can be fixedly mounted to the tubular member 12. A supply 64 of suture material 30 mounted within reel assembly 65 is coupled thereby to rod 62 through opposed flanges 66 (FIG. 1C) and pin 56. Manually or automatically-operable provisions for advancing suture material from the supply reel 65 can be provided. In the arrangement depicted in FIG. 1, a hand-operated crank 67 coupled to the supply reel 65 through a conventional spring release assembly, designated generally by reference numeral 68, can be provided to control the advancement of suture material between inlet rollers 54a and 54b. The spring release assembly 68 can be of the type which provides a spring resistance to rotation of the reel 65 unless the reel 65 is displaced laterally with respect to flanges 66 to prevent inadvertent release of suture material from the reel 65, or can be coupled to an automatically operable device such as a spring motor (not shown) that is wound upon rotation of the handle of a winding device 67 in a predetermined direction. Alternatively, the winding handle 67 and any related winding apparatus can be arranged so as to be operable with respect to one or both of intake rollers 54a, 54b (FIG. 13) in order to provide for automatic or manual advancement of suture material into an appropriate one of the inner tubular members 34a, 34b. It is to be appreciated that advancement of suture material in any of the above-described manners advances suture material through one of the inner inlet tubular members, such as 34b, through corresponding forcep arm 24b so as to extend into and through opposed forcep arm 24a and return proximally through inner tubular member 34a to emerge between opposed outlet rollers 60a and 60b for further manipulation, such as future knot tying. Alternative roller arrangements to that depicted in FIG. 1 can be provided for the advancement of suture material. For example, single inlet and outlet rollers 54a, 60a (FIG. 1F) can be provided in lieu of the multiple roller arrangement of FIG. 1. The spring release and crank assembly can be mounted to the inlet roller 54a as shown, or to the reel 65 in the manner described above to control the supply of suture material to the forcep assembly 18 in the manner described above.

Alternative configurations and modes of operation for the suture material advancing means 22 can be substituted for the handle and crank assembly described above. For example, suitable DC-powered or spring-powered motor assemblies can be provided to advance the suture material distally through the forcep arms 24a and 24b in a continuous manner until disengagement of motor actuation in the case of the DC-motor or uncoupling of the spring motor from the suture supply reel. Such "automated" suture advancing systems may be particularly advantageous in configurations of the suture instrument 10 in which the outer tube 12 thereof is provided with a length of on the order of about 30 cm or longer so as to minimize operator fatigue and expedite the suturing process. Alternatively, the suture material can be manually advanced into the outer tubular member 12 by configuring the supply reel 65 as a thumb-roller in frictional engagement with the inlet roller 54b and the outlet roller 60b such that rotation of the reel roller 65 directs relative movement of the respective inlet rollers 54a, 54b so as to draw suture material therebetween from the reel 65 to advance the suture material distally, through the forceps 24a, 24b, and outwardly therefrom to exit the instrument 10 between outlet rollers 60a, 60b. Advancement of suture material is terminated upon the user's cessation of operation of the thumb roller 65, thereby providing the user with a high degree of control as to the amount and rate of suture material advancement through the instrument.

FIGS. 14A-14D illustrate schematic form formation of a suture with the instrument. Two or more tissue or organ segments to be sutured, designated T1 and T2 throughout the drawings, are positioned between the open forcep arms 24a and 24b and are pierced thereby upon closure of the forcep arms, as illustrated in FIG. 14A in the manner described above. Suture material 30i is advanced distally toward the tissue T1, T2 through one of the forcep arms (forcep arm 24b in the drawings), through the opposed forcep arm (24a), and returns proximally, as illustrated in FIG. 14B, preferably through the corresponding inner tubular member 34a (FIGS. 11 and 12A). Following extension of the suture material through the tissue segments T1 and T2, the forcep arms are separated from one another and removed from the tissue, leaving a loop 30L of suture material extending between the tissue segments T1 and T2. As the forcep arms 24a, 24b are withdrawn from the tissue segments, suture material can be advanced by way of any one of the foregoing suture advancing arrangements through the instrument and tissue segments in the direction of the arrows (FIG. 14C). Once the instrument has been removed from the suture site, a surgical knot 31 (FIG. 14D) can be tied in the suture material, advanced to the tissue segments, and appropriately tensioned to join the tissue segments together, as shown in FIG. 14E.

A device 70 that is helpful in advancing the suture knot 31 to the tissue segments T1 and T2 is illustrated schematically in FIGS. 15A and B. The knot advancing device comprises an elongated tubular structure 72 having formed therein a longitudinal slot 74 which extends from the distal end 76 to the proximal end 78 of the device. A knob 79 detachably mounted at the proximal end of the device includes means such as an angularly extending slot 81 for receiving the suture material from the groove. A recess 80 formed at the distal end of the device 70 is provided for receiving the knot 31 therein. The device recess 80 is advanced distally against the knot 31, and the outwardly-extending length of suture material 30o is pulled along groove 74 and along slot 74 as the knob 79 is advanced proximally, as indicated in phantom, to advance the suture knot into a desired tensioned engagement with tissue segments T1 and T2 joined by the suture loop 30L.

Figure 16:
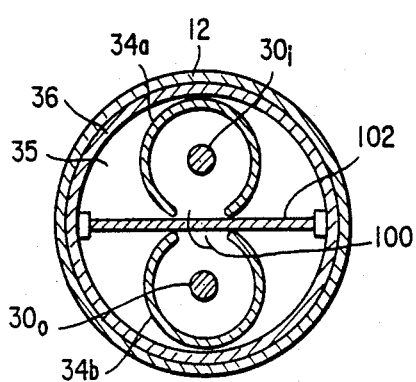
FIGS. 16 and 17 are cross-sectional views of an alternative aspect of a portion of the instrument depicted in FIG. 1.
Figure 17:
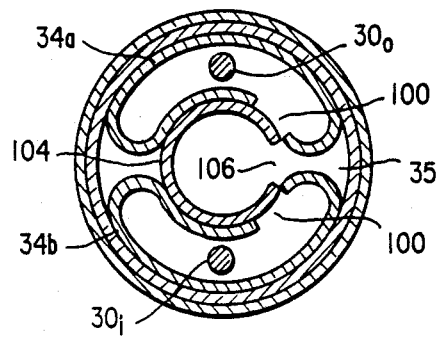

In an alternative configuration of the instrument 10, as illustrated in FIGS. 16 and 17, the inner tubular members 34a and 34b are each provided with a generally "C"-shaped or "U"-shaped cross-sectional configuration (FIG. 16), or an open-sided crescent-shaped configuration (FIG. 17) so as to provide a longitudinally extending channel 100 extending into the cavity 35 of the outer tubular member. The channels 100 are dimensioned so as to permit passage therethrough of suture material 30o and 30i. The channels 100 can be closed off by suitable obstructing means such as a plate member 102 (FIG. 16) or a rotatable rod 104 having a generally "C" or "U"-shaped cross-section so as to define a lumen 106 for receiving suture material strands 30i and 30o. Removal of plate 102 or rotation of rod 104 such that the rod lumen opening faces the channels 100 permits for displacement of the suture material from the inner tubular members 34a, 34b into the cavity 35 of the outer tubular member, thereby permitting insertion of device 70 into the cavity 35 following suture knot formation so as to advance the suture knot 31 toward the tissue segments T1 and T2 (FIGS. 14A-14D) through the instrument cavity 35. In an alternative arrangement, the plate 102 can be configured as a suture knot advancing device 70' that can be removably mounted within the instrument cavity 35, as illustrated in FIGS. 18 and 19. The device 70' is configured as a generally rod-like structure having a pair of opposed, generally U-shaped recesses 110 formed therein which substantially surround the tubular members 34a and 34b when the device 70' is received within the instrument cavity 35. A longitudinal slot 74' which extends from the distal end of the device 70' to the proximal end of the device is provided to receive the outwardly-extending portion of the suture material following trying of the suture knot. The slot 74' extends from the outer surface of the device 70' medially toward the longitudinal center of the device, where the slot terminates at an enlarged recess 75'. The recess 75' terminates at knot-receiving recess 80' at the distal end of the device. A detachable knob of the type discussed above in connection with FIGS. 15A and 15B can be provided to facilitate suture knot advancement toward the tissue segments to be joined.

In use, the knot advancing device 70' is removed from the suture instrument 10 following advancement of suture material through the tissue segments in the manner described above and illustrated schematically for one aspect of the invention in FIGS. 14A-14E. Once one or more knots have been tied in the suture material, the device 70' is brought alongside the suture material such that the outwardly-extending portion of suture material 30o is positioned within slot 74' and the suture material knot 31 is received within the knot-receiving recess 80' of the device 70'. The device 70' and accompanying knot 31 is re-inserted within the instrument cavity 35 and advanced distally, past the open forcep arms 24a and 24b to an appropriate, tensioned position adjacent the tissue segments to be joined by the suture material.

The foregoing detailed description is illustrious of various embodiments of the suture tying instrument of the subject invention. It will be appreciated from the foregoing description that variations and changes that can be made to the invention as set forth hereinabove and in the accompanying drawings expressly intended to be encompassed by this description and the accompanying claims.

What is claimed is:

1. A surgical suture device, comprising:
a cylindrical tubular member defining a cavity extending from a distal end of the tubular member toward a proximal end of the tubular member;
a forcep assembly comprising at least two opposed jaw members, at least one of said jaw members being selectively displaceable with respect to said tubular member, each of said jaw members defining a lumen in fluid communication with said tubular member cavity;
means for selectively displacing said at least one displaceable jaw member; and
means for advancing suture material through said opposed jaw members so as to extend within said tubular member cavity following passage through said jaw members.

2. The device according to claim 1, wherein said tubular member is configured as an outer tubular member defining at least one inner tubular member extending between one of said jaw members and the proximal end of the outer tubular member.

3. The device according to claim 1, wherein said tubular member is configured as an outer tubular member defining at least two inner tubular members, one of said inner tubular members extending between each of said jaw members and the proximal end of the outer tubular member.

4. The device according to claim 3, wherein each of said inner tubular members is provided with a longitudinally-extending channel open toward said outer tubular member cavity.

5. The device according to claim 4, wherein said inner tubular member channels are oriented so as to face one another.

6. The device according to claim 5, further comprising means for closing off at least one of said inner tubular member channels.

7. The device according to claim 6, wherein said inner tubular channel closing off means is selectively removable from the tubular member cavity.

8. The device according to claim 7, further comprising means insertable between said inner tubular member channels for advancing a suture material knot toward said forcep assembly.

9. The device according to claim 8, wherein said suture knot advancing means comprises an elongated member having a recess formed at one end thereof for receiving the suture material knot.

10. The device according to claim 9, wherein said knot advancing means further comprises a slot that extends medially from an outer surface of the member for receiving suture material extending from said suture knot.

11. The device according to claim 10, wherein the elongated member is generally symmetrical along its longitudinal axis.

12. The device according to claim 4, wherein said inner tubular member channels are selectively alignable with one another.

13. The device according to claim 4, wherein each of said inner tubular members is provided with a generally crescent-shaped across-sectional configuration.

14. The device according to claim 4, wherein each of said inner tubular members is provided with generally circular cross section.

15. The device according to claim 3, wherein said inner tubular members are detachably mounted within said other tubular member.

16. The device according to claim 1, wherein each of the opposed jaw members is selectively displaceable relative to said tubular member.

17. The device according to claim 1, wherein each of said jaw members is provided with a sharp-edged distal tip and the opposed jaw members are displaceable relative to one another between an open and a closed position.

18. The device according to claim 17, wherein one of said opposed jaw member distal tips is insertable in the lumen of the distal tip of its opposed jaw member cavity to said jaw member distal tip insertable into said opposed jaw member lumen.

19. The device according to claim 18, wherein said suture advancing means includes means for advancing suture material distally through said tubular member.

20. The device according to claim 17, wherein said opposed distal tips are positionable adjacent one another in close proximity when said jaw members are oriented in the closed position.

21. The device according to claim 20, wherein said jaw member distal tips are angled relative to one another in partially overlapping relationship so as to facilitate tissue piercing upon closing of the jaw members.

22. The device according to claim 21 wherein said opposed jaw member distal tips are angled in opposite directions relative to one another.

23. The device according to claim 21, wherein said opposed jaw member distal tips are angled in substantially similar directions.

24. The device according to claim 1, wherein said jaw member displacing means comprises a handle assembly operable by a user to selectively extend and retract said at least one displaceable jaw member relative to its opposed jaw member.

25. The device according to claim 24, wherein said handle comprises a proximal handle member and a distal handle member, said at least one displaceable jaw member being coupled to one of said handle and the tubular member being coupled to the outer of said handle members.

26. The device according to claim 25, wherein said proximal and distal handle members are coupled to one another by a spring arm.

27. The device according to claim 26, further comprising means for selectively fixing the relative position of said proximal and distal handle members.

28. The device according to claim 25, wherein said proximal and distal handle members are configured as scissor handle members that are pivotably connected to one another.

29. The device according to claim 28, further comprising biasing means for urging said scissor handle members toward a predetermined orientation.

30. The device according to claim 28, further comprising means for selectively fixing the relative position of said scissor handle members.

31. The device according to claim 25, wherein said at least one displaceable jaw member includes means extending through said tubular member cavity for coupling with said respective handle member to effect displacement of the displaceable jaw member.

32. The device according to claim 30, wherein both of said jaw members are selectively displaceable, said inner tubular members being coupled to its respective handle member to effect jaw member displacement upon manipulation of said handle members relative to one another.

33. The device according to claim 31, wherein said means extending through said tubular member cavity comprises an inner tubular member through which suture material is advanceable to said lumen of said at least one displaceable jaw member.

34. The device according to claim 33, wherein said proximal handle member is coupled to said inner tubular member and said distal handle member is coupled to said outer tubular member.

35. The device according to claim 33, wherein said inner tubular member is telescopically extensible within said outer tubular member.

36. The device according to claim 33, further comprising a second inner tubular member extending between the lumen of the other of said opposed jaw members through which suture material is advanceable.

37. The device according to claim 1, wherein said suture material advancing means is detachably mounted to the proximal end of the tubular member.

38. The device according to claim 1, wherein said suture material advancing means comprises means for advancing suture material through the tubular member cavity to one of said forcep jaw members.

39. The device according to claim 38, wherein said suture material advancing means comprises a reel assembly through which suture material can be passed that is selectively operable to advance suture material into said tubular member cavity.

40. The device according to claim 39, further comprising self-powered means for operating said reel assembly.

41. The device according to claim 39, wherein said reel assembly comprises a suture supply reel and at least one pair of opposed roller wheels cooperable with said supply reel to advance suture material through the suture device.

42. The device according to claim 1, wherein at least one of the opposed jaw members is provided with a longitudinally extending slot that extends into said lumen.

43. The device according to claim 1, wherein at least one of said opposed jaw members is provided with an umbricated, concave recess formed at the distal end of the respective jaw member.

44. The device according to claim 1, wherein the device is configured as a reusable instrument that is disassembleable to facilitate instrument cleaning and sterilization.

45. The device according to claim 1, wherein said forcep assembly is selectively retractable within said tubular member.

46. A method for suturing tissue at a surgical site, comprising the steps of:
    positioning a suturing instrument adjacent the tissue to be sutured, the suturing instrument having at least two opposed forcep jaw members, at least one of the jaw members being displaceable relative to an instrument body and being selectively operable to move between a forcep open position and a forcep closed position, each of the opposed jaw members defining a lumen extending therethrough;
    interposing the tissue to be sutured between the opposed jaw members and urging the displaceable jaw member toward its opposed jaw member to the closed position such that at least one of the jaw members penetrates the tissue to be sutured;
    advancing suture material through the opposed jaw members so as to extend through the tissue to be sutured;
    urging opposed jaw members of said forceps to said open position;
    tying a knot in the suture material; and advancing the suture knot toward the tissue to be sutured.

47. The method according to claim 46, further comprising the step of advancing the suture knot through the instrument body to the tissue to be sutured.

48. The method according to claim 46, further comprising the step of inserting a distal tip of one of the jaw members into the lumen of the other of the opposed jaw members.

49. The method according to claim 48, further comprising the step of advancing the suture material through the lumen of the inserted jaw member and into the lumen of the opposed jaw member.

50. The method according to claim 46, further comprising the step of actuating suture self-advancing means to advance suture material through the opposed jaw members.

51. The method according to claim 42, wherein the suturing instrument is removed from the tissue to be sutured prior to trying of the suture knot.

52. The method according to claim 46, wherein the suture knot is tied prior to removal of the suturing instrument.

53. A device for advancing a knot formed in suture material toward tissue to be sutured, the device comprising an elongated member and a detachable end cap having means for receiving suture material, said elongated member having a knot-receiving recess formed at one end thereof and a longitudinally-extending slot which extends medially from an outer surface of the elongated member.

54. The device according to claim 53, wherein said slot extends from said knot-receiving recess.

55. The device according to claim 54, wherein the device is generally symmetrical about its longitudinal axis.

* * * * *